(12) United States Patent
Valley

(10) Patent No.: US 9,665,931 B2
(45) Date of Patent: *May 30, 2017

(54) AIR POCKET DETECTION METHODS AND SYSTEMS

(71) Applicant: SunEdison Semiconductor Limited (UEN201334164H), Singapore (SG)

(72) Inventor: John F. Valley, Lake Oswego, OR (US)

(73) Assignee: SunEdison Semiconductor Limited (UEN201334164H), Singapore (SG)

( * ) Notice: Subject to any disclaimer, the term of this patent is extended or adjusted under 35 U.S.C. 154(b) by 901 days.

This patent is subject to a terminal disclaimer.

(21) Appl. No.: 13/712,561

(22) Filed: Dec. 12, 2012

(65) Prior Publication Data

US 2013/0176454 A1 Jul. 11, 2013

Related U.S. Application Data

(60) Provisional application No. 61/580,900, filed on Dec. 28, 2011.

(51) Int. Cl.
*H04N 9/47* (2006.01)
*H04N 7/18* (2006.01)
(Continued)

(52) U.S. Cl.
CPC ........... *G06T 7/0002* (2013.01); *G01N 21/00* (2013.01); *G01N 21/59* (2013.01); *G01N 21/88* (2013.01);
(Continued)

(58) Field of Classification Search
CPC ............................................ G06T 2207/30148
(Continued)

(56) References Cited

U.S. PATENT DOCUMENTS 7,728,969 B2 6/2010 Saito et al.
7,912,658 B2 3/2011 Biellak et al.
(Continued)

FOREIGN PATENT DOCUMENTS

JP 2007071791 A 3/2007
JP 2007258555 A 10/2007
(Continued)

OTHER PUBLICATIONS

National Instruments, "Image Analysis and Processing," May 15, 2008, located at www.ni.com, 6 pages.
(Continued)

*Primary Examiner* — Hung Dang
*Assistant Examiner* — Girumsew Wendmagegn
(74) *Attorney, Agent, or Firm* — Armstrong Teasdale LLP

(57) ABSTRACT

Methods and systems for use in detecting an air pocket in a single crystal material are described. One example method includes providing a matrix including a plurality of data units, the plurality of data units including image data related to a region of interest of the single crystal material; determining, by a processor, a difference between data units of the matrix and a corresponding data unit of the matrix, wherein the corresponding data unit is defined by a first operation of the matrix; calculating, by the processor, a first index value based on the differences of the corresponding data units; and identifying an air pocket within the single crystal material based on the first index value and a predetermined threshold.

24 Claims, 5 Drawing Sheets

(51) Int. Cl.
| | |
|---|---|
| G06T 7/00 | (2017.01) |
| G01N 21/00 | (2006.01) |
| G06F 17/10 | (2006.01) |
| G06T 7/60 | (2017.01) |
| G01N 21/59 | (2006.01) |
| G01N 21/88 | (2006.01) |
| G01N 21/95 | (2006.01) |
| G06T 7/68 | (2017.01) |
| H01L 21/66 | (2006.01) |
| G01N 21/84 | (2006.01) |

(52) U.S. Cl.
CPC ......... *G01N 21/9505* (2013.01); *G06F 17/10* (2013.01); *G06T 7/0004* (2013.01); *G06T 7/608* (2013.01); *G06T 7/68* (2017.01); *G01N 2021/5957* (2013.01); *G01N 2021/8477* (2013.01); *G06T 2207/10048* (2013.01); *G06T 2207/30148* (2013.01); *H01L 22/12* (2013.01)

(58) Field of Classification Search
USPC ........................................ 382/149; 348/222.1
See application file for complete search history.

(56) References Cited

U.S. PATENT DOCUMENTS

| | | | |
|---|---|---|---|
| 8,114,215 B2 | 2/2012 | Song et al. | |
| 8,269,960 B2 | 9/2012 | Reich et al. | |
| 8,284,394 B2 | 10/2012 | Kirk et al. | |
| 2003/0149947 A1* | 8/2003 | Sarig | 716/4 |
| 2009/0120353 A1 | 5/2009 | Korb et al. | |
| 2011/0013016 A1 | 1/2011 | Tillotson | |
| 2011/0224932 A1 | 9/2011 | Huet et al. | |
| 2012/0132131 A1 | 5/2012 | Song et al. | |
| 2012/0141808 A1 | 6/2012 | Song et al. | |

FOREIGN PATENT DOCUMENTS

| | | |
|---|---|---|
| JP | 2008102027 A | 5/2008 |
| WO | 2005017832 A1 | 2/2005 |

OTHER PUBLICATIONS

Tsai, C.K., APIS Introduction (Automatic Pin-Hole Inspection System) (KEMET/HANTEC, HAPI-300-2F), 24 pages.

De Bisschop, Peter, et al., "Simulation of the effect of a resist-surface bound air bubble on imaging in immersion lithography," Proceedings of SPIE, vol. 5754, May 12, 2005, pp. 243-253.

International Search Report and Written Opinion issued in Application No. PCT/US2012/070169, mailed Mar. 25, 2013.

Image Analysis and Processing, Tutorial, National Instruments, May 15, 2008, pp. 6.

* cited by examiner

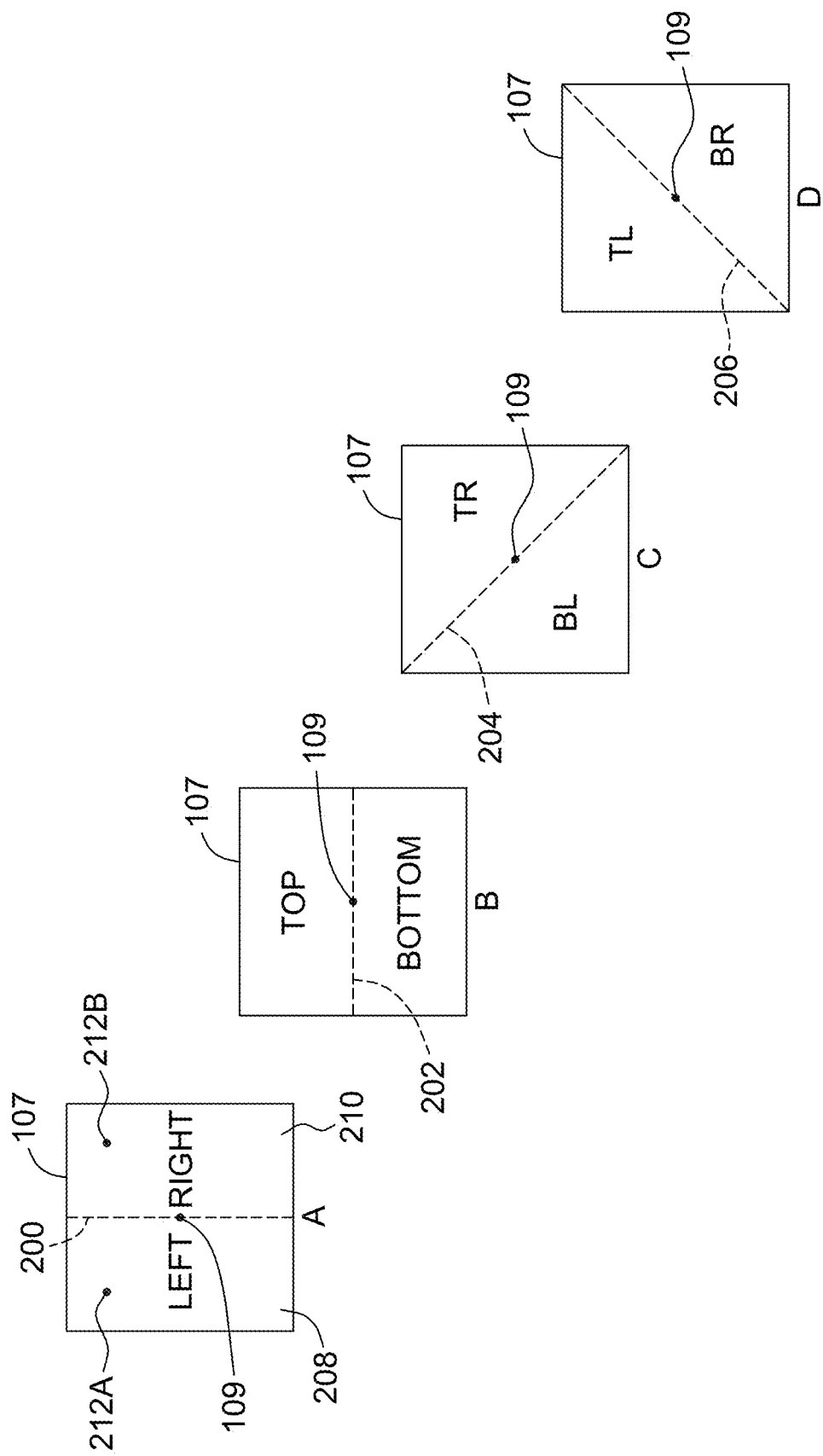

AIR POCKET DETECTION METHODS AND SYSTEMS

CROSS-REFERENCE TO RELATED APPLICATIONS

This application claims priority to U.S. Provisional Application No. 61/580,900 filed Dec. 28, 2011, the entire disclosure of which is hereby incorporated by reference in its entirety.

FIELD

This disclosure relates generally to air pocket detection systems and methods and, more specifically, to detection of one or more air pockets in a single crystal material based on the symmetry of an image object within a region of interest of the material.

BACKGROUND

Single crystal ingots, such as silicon ingots, are grown and processed into semiconductor wafers. During processing, one or more tests or inspections may be performed to determine if one or more air pockets (e.g., voids) exist within the ingot, before and/or after slicing into wafers. Detection of the air pocket early in the processing is desired to avoid further processing of portions of the ingot having the air pocket, because the air pocket may affect the structural integrity of the ingot and/or usefulness of the ingot in one or more products. Detection of air pockets prior to shipment of product wafers may be required to prevent failure of the wafer at some future processing, such as during manufacturing of a semiconductor and/or photovoltaic device.

This section is intended to introduce the reader to various aspects of art that may be related to various aspects of the disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

In one aspect of the present disclosure, a computer-implemented method for use in detecting an air pocket in a single crystal material is provided. The method includes providing a matrix including a plurality of data units, the plurality of data units including image data related to a region of interest of the single crystal material; determining, by a processor, a difference between data units of the matrix and a corresponding data unit of the matrix, wherein the corresponding data unit is defined by a first operation of the matrix; calculating, by the processor, a first index value based on the differences of the corresponding data units; and identifying an air pocket within the single crystal material based on the first index value and a predetermined threshold.

Another aspect of the present disclosure is a detection system for use in detecting an air pocket in a material. The detection system includes a light source configured to emit near-infrared (NIR) light toward a material, a detection device positioned adjacent to the material to capture image data based on light passing through the material, and a processor coupled to the light source and the detection device. The processor is configured to identify a square matrix including a plurality of data units, determine a difference between data units of the matrix and corresponding data units of the matrix, calculate a first index value based on the differences of the corresponding data units; and identify an air pocket within the single crystal material based on the first index value and a predetermined threshold. The plurality of data units includes the image data related to a region of interest of the single crystal material, and the corresponding data units are defined by a first operation on the matrix.

Yet another aspect of the present disclosure is one or more non-transitory computer-readable storage media having computer-executable instructions embodied thereon. When executed by at least one processor the computer-executable instructions cause the at least one processor to identify a matrix including a plurality of data units, determine a difference between data units of the matrix and corresponding data units of the matrix, calculate a first index value based on the differences of the corresponding data units, and identify an air pocket within the single crystal material based on the first index value and a predetermined threshold. The plurality of data units includes image data related to a region of interest of the single crystal material, and the corresponding data units are defined by a first operation on the matrix.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

FIG. 5 is a block diagram illustrating four exemplary axes of the material of FIG. 2.

Corresponding reference characters indicate corresponding parts throughout the drawings.

DETAILED DESCRIPTION

The systems described herein are operable to detect light passing through a single crystal material, such as a single crystal sample, and process the image data based on the detected light to determine if an air pocket (APK) is present within the material. Generally, APK anomalies (e.g., voids) define substantially circular shapes, while non-APK anomalies deviate from a circular shape. As such, the systems described herein determine the symmetry of the intensity of image data for a material to discriminate between APK and non-APK anomalies in the material.

In one embodiment, technical effects of the methods, systems, and computer-readable media described herein include at least one of: (a) providing a matrix including a plurality of data units, the plurality of data units including image data related to a region of interest of the single crystal material, (b) determining, by a processor, a difference between data units of the matrix and corresponding data units of the matrix, wherein the corresponding data units are defined by a first operation on the matrix, (c) calculating, by the processor, a first index value based on the differences of the corresponding data units, and (d) identifying an air pocket within the single crystal material based on the first index value and a predetermined threshold.

Figure 1:
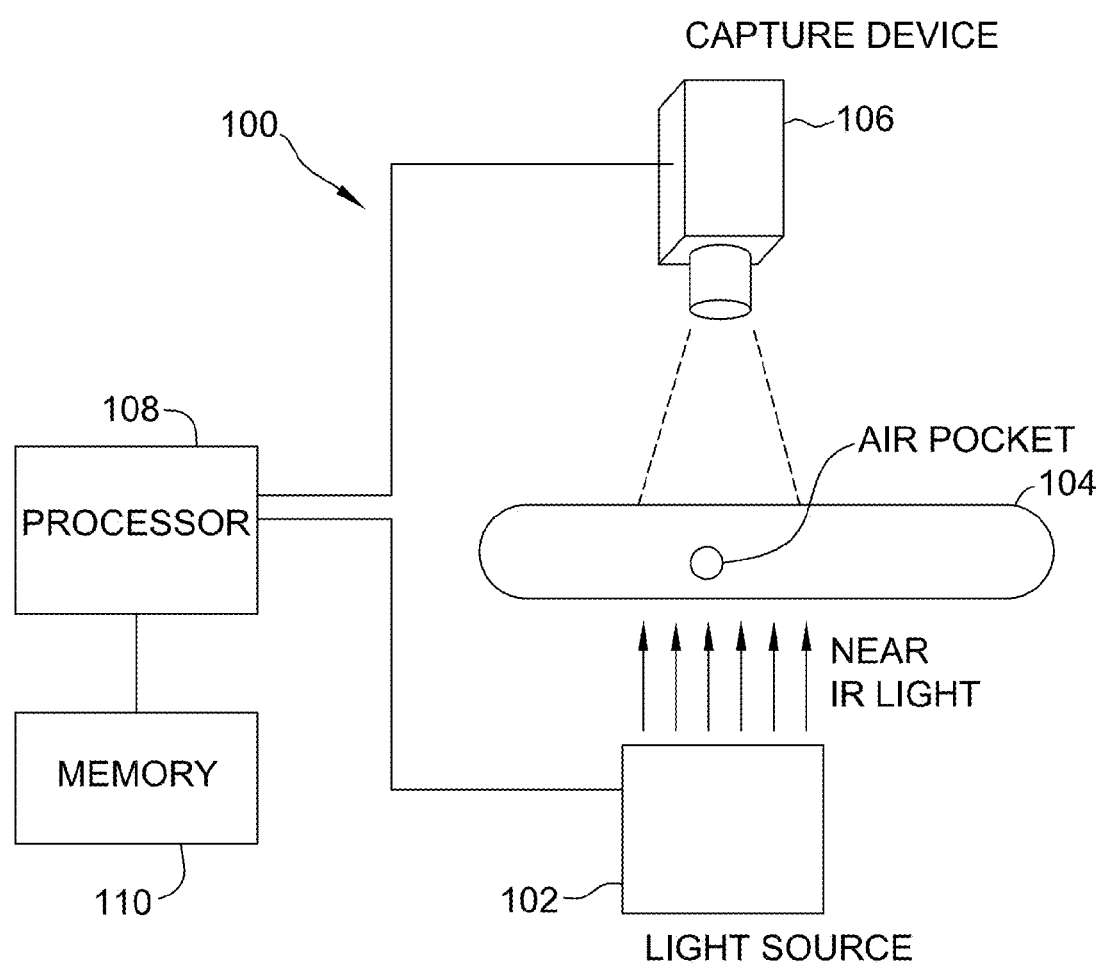
FIG. 1 is a block diagram of an exemplary detection system.

Referring to the drawings, an exemplary detection system is shown in FIG. 1 and indicated generally at 100. In this embodiment, detection system 100 includes a light source 102, such as a near-IR or near-infrared light source, to direct light toward a material 104. The light source 102 is configured to provide light, which defines a wavelength sufficient to penetrate the material 104. In various embodiments, the wavelength of the light from light source 102 (e.g., near-infrared (NIR) light) is selected based on the thickness of the material 104. In one example, the wavelength of the near-IR light emitted from the light source 102 is about 1 to about 2 microns. It is contemplated, however, that light having one or more different wavelengths can be emitted from light source 102.

On the opposite side of the material 104, the detection system 100 includes a capture device 106 configured to capture the light passing through the material 104. In this example, the image capture device 106 is a camera, such as a silicon-based CCD or CMOS array camera. In another example, the capture device 106 includes an InGaAs MOS array camera. Image arrays contemplated herein are two dimensional. Further, one dimensional line-scan or two dimensional time-delay integration (TDI line-scan) cameras with mechanized scanning may be used to create the two dimensional image arrays, while standard two dimensional array "snap shot" cameras may also be used. Single capture devices 104 may also be employed, which are used to create two dimensional images using a Nipkow disk or other method to scan an image across a single capture devices or series of discrete capture devices. More generally, a variety of different types of capture devices 106 configured to capture light at the particular wavelength emitted by the light source 102 and transmitted through the material 104 are possible for this application. The capture device 106 is provided to generate two dimensional image data, which is substantially in-focus and representative of light passing through the material 104. The image data may be provided in a single image or multiple images. Multiple images can be provided as multiple image slices of the material 104, at different depths of the material 104, or from different perspectives, such as viewing or illumination angle.

The material 104 may include various different types of materials, such as silicon, germanium, gallium arsenide, or other types of materials formed through a crystalline process. In this embodiment, the single crystal material 104 is a Czochralski (CZ) grown material forming one or more ingot sections, slices, wafers, slugs, slabs, and/or cylinders. The material 104 shown in FIG. 1 is nominally plain parallel, such that the top surface is generally parallel with the bottom surface of the material 104. In other examples, a material may be nearly plain parallel or non-plain parallel, such as cylindrical ingot sections.

In this embodiment, the single crystal material 104 may be subjected to testing at detection system 100 in a variety of conditions, including, for example, potentially doped with various dopants to some level, crude (such as slabs or slugs or after slicing, grinding, lapping or etching), polished (e.g., SSP wafer having front side only polished, back side in various conditions or DSP wafer having both surfaces polished, with front surface potentially final or kiss polished), and/or coated with an epitaxial layer of the same single crystal material except, potentially, a different doping level. Materials 104 may be provided in a variety of thicknesses, such as, for example, from under 1 mm up to about 10's of mm, or other thickness directly from a growing process or after one or more processing steps.

Detection system 100 further includes a processor 108 and a memory 110 coupled to the processor 108. Processor 108 may include one or more processing units (e.g., a multi-core configuration). The term processor, as used herein, refers to central processing units, microprocessors, microcontrollers, reduced instruction set circuits (RISC), application specific integrated circuits (ASIC), logic circuits, and/or any other circuit or processor capable of executing instructions to perform functions described herein. Further, processor 108 may include separate discrete devices located proximate to one another, and/or remotely from one another.

Memory 110 is one or more devices operable to enable information such as executable instructions and/or other data to be stored and/or retrieved. Memory 110 may include one or more computer readable media, such as, without limitation, hard disk storage, optical drive/disk storage, removable disk storage, flash memory, non-volatile memory, ROM, EEPROM, random access memory (RAM), etc. In several examples, memory 110 includes one or more non-transitory computer-readable storage media configured to store, without limitation, computer-executable instructions, image data, predetermined thresholds, and/or any other types of data referred to herein, expressly or inherently. Memory 110 may be incorporated into and/or separate from processor 108, and/or accessible through one or more networks (e.g., Cloud storage).

As used herein, the term "region of interest" may refer to any image region, including binary image or gray-scale image regions, that includes one or more image objects or blobs. As used herein, the term "image object" and "blob" may refer to, for example, data units of which at least a portion are being evaluated by the methods and systems described herein. In some embodiments, the term "image object" may refer to data units within a grey-scale image, while the term "blob" may refer to data units within a binary image.

In use, the single crystal material 104 is positioned between the light source 102 and the capture device 106, such that light from the light source 102 is directed through the material 104, and captured by capture device 106, potentially requiring scanning of the material 104 or the image capture device 106 to produce the captured two dimensional image array. The image data generated by the capture device 106 is provided to processor 108, which stores the image data in memory 110. Example image data of materials captured by capture device 106 is illustrated in FIGS. 2A-4A. The systems and methods described herein are provided to process the image data to determine if one or more APKs are present in the material 104.

In this embodiment, the image data is processed to provide a matrix of data units (e.g., picture elements or pixels) representative of a region of interest (e.g., an anomaly) of the image data. In one example, processor 108 inverts the intensity of the image data according to one or more thresholds, as shown in FIG. 2B-4B. The processing provides an image object of pixels (e.g., a blob), which are representative of an anomaly within the material 104. The processor 108 identifies the anomalies as regions of interest, such as region of interest 114 of FIG. 2A, which may contain an APK. In at least one embodiment, processor 108 may or may not apply one or more initial processes to identify larger, more easily identified APKs, while other methods herein may be used to identify APKs and APK-like anomalies. For example, larger APKs or anomalies not resembling APKs may be identified during imaging of the material 104 by capture device 106, such as a line-scan or TDI line-scan camera. Further, in various embodiments, the processor 208 may initially perform one or more other operations on the image data, such as filtering, inverting, or other operation to provide more efficient processing of the image data according to the methods provided herein.

Figure 2A:
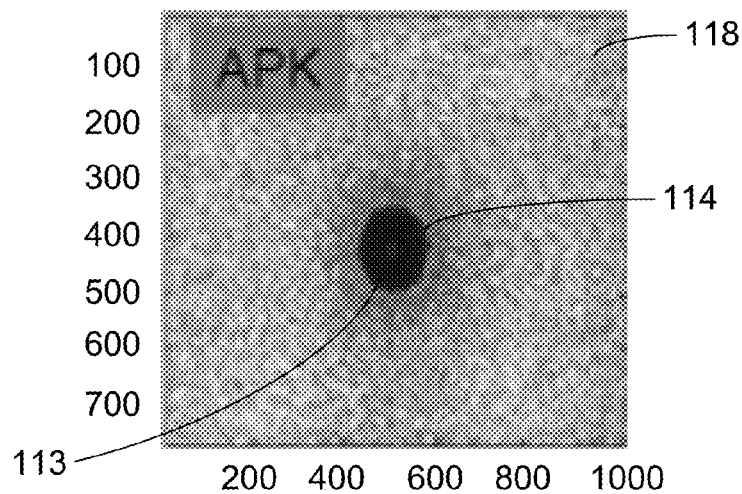
FIGS. 2A, 2B, and 2C illustrate image data for a material having an air pocket (APK) anomaly.
Figure 2B:
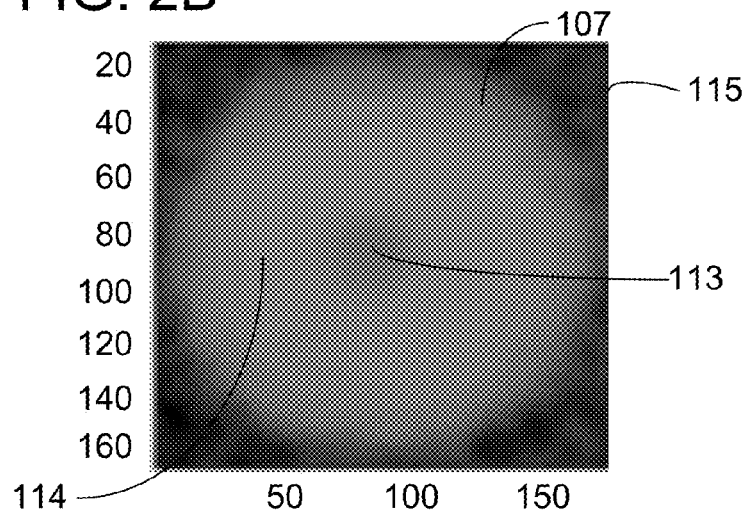
Figure 2C:
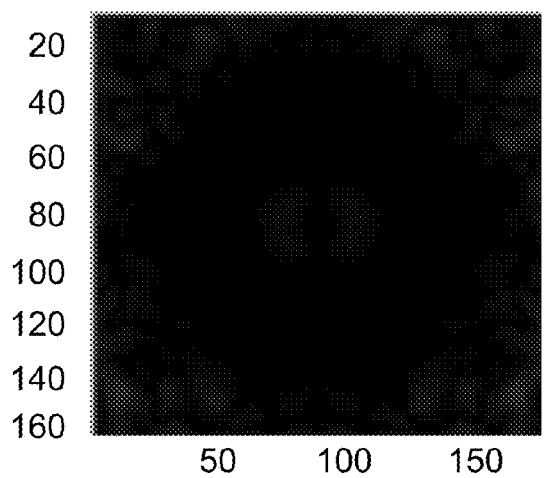
Figure 3A:
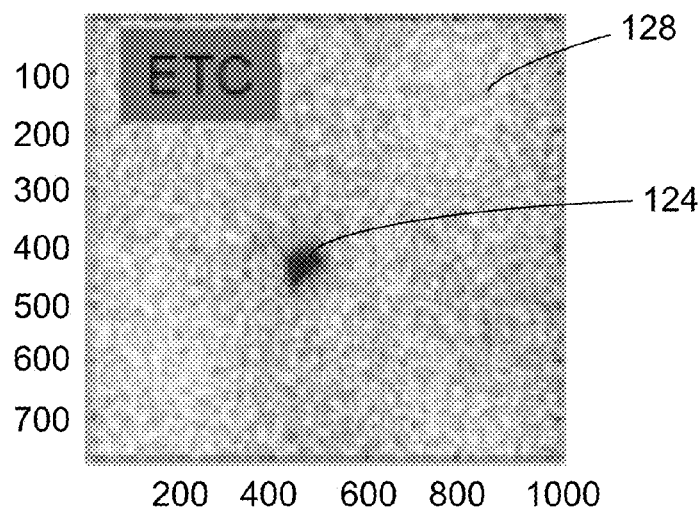
FIGS. 3A, 3B, and 3C illustrate image data for a material having a non-APK anomaly.
Figure 3B:
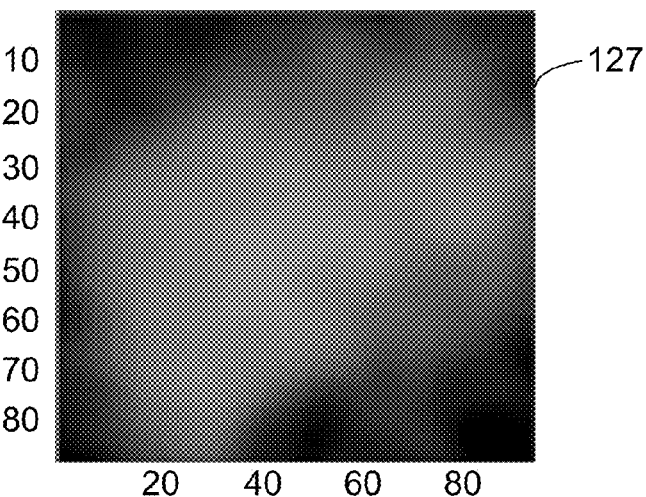
Figure 3C:
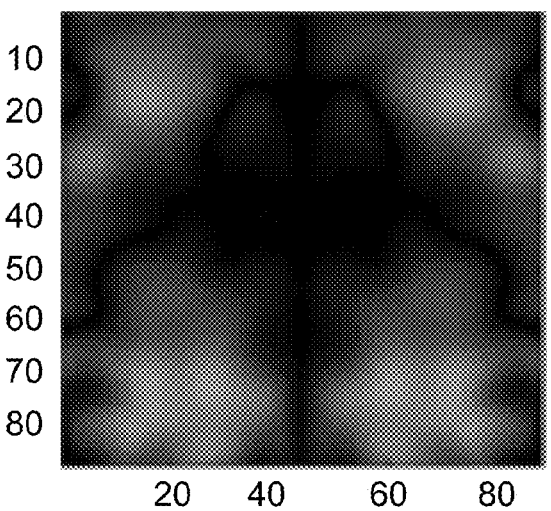
Figure 4A:
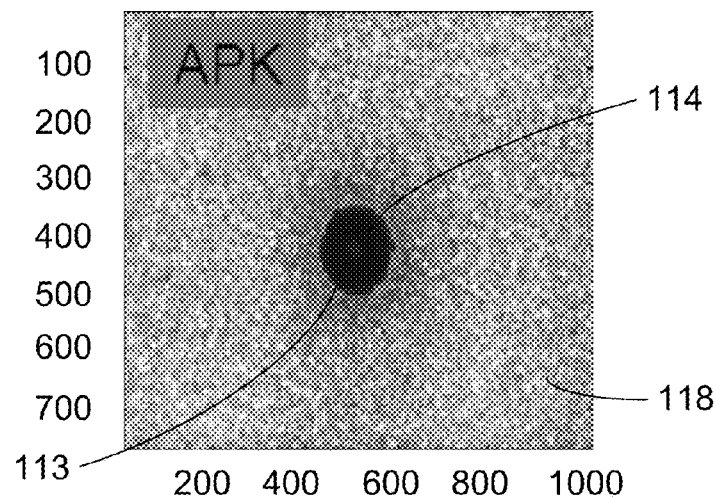
FIG. 4A, 4B, and 4C illustrate image data for a material having an APK anomaly, with a mask applied to the matrix.
Figure 4B:
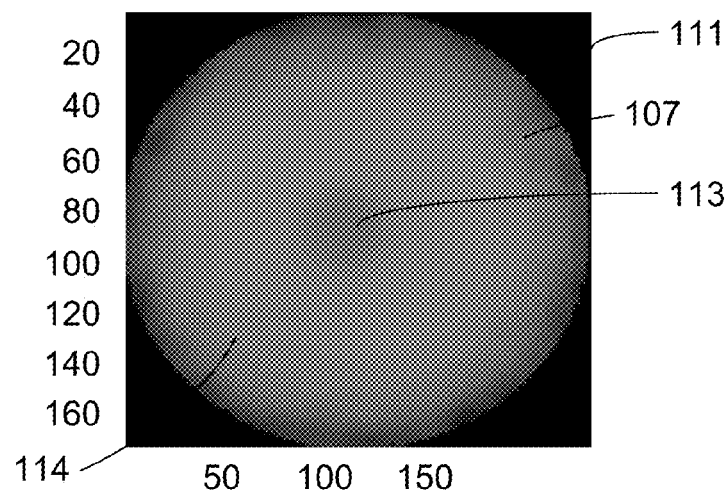
Figure 4C:
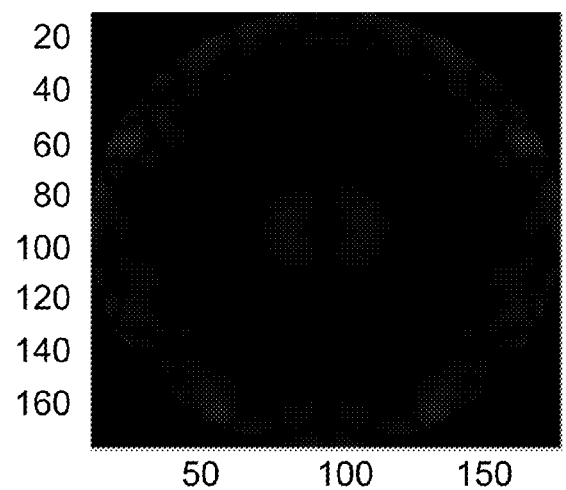

Upon detection of a region of interest, the processor 108 defines a matrix of data units including at least one portion of the image indicating the image object. In the illustrated examples, the processor 108 provides the matrix 107 and 127 of gray-scale data units including the image objects 114 and 124, as shown in FIGS. 2B and 3B, respectively. In the examples, the matrixes 107 and 127 are squares. In other embodiments, a matrix may include a different shape, which is generally symmetrical over at least one axis. The size of the matrix can potentially be padded to include pixels outside the found image object or clipped to remove the outermost pixels of the image object prior to further processing. The threshold processing and/or other processing methods may be further employed to improve the image quality of the regions of interest with respect to background noise. Further, a mask may be applied to the image data based on a best-fit circle, best-fit ellipse or threshold boundary positioned over the region of interest. In the example of FIG. 4, a circle mask 111 is applied to the region of interest 114 to limit noise and other affects outside of the mask 111. In the example embodiment, the processor 108 sets the data units (e.g., pixels) outside the mask 111 to zero intensity or black. It should be appreciated that various different types and shapes of masks (e.g., ellipse, circle, image object threshold boundary) may be used in a variety of embodiments to enhance the efficiency and/or accuracy of the detection system 100. In other embodiments, such as shown in FIGS. 2 and 3, a mask may be omitted or may include multiple weighting levels.

As shown in FIG. 2, the matrix 107 is located on the image object 114 within the image data. The image object 114 generally includes a center 113, and processor 108 centers the matrix 107 substantially on the center 113 of the image object 114. In one example, a matrix is centered on the image object through use of bi-linear and/or bi-cubic interpolation. More specifically, one or more interpolation algorithms may be applied to the existing data units within the matrix, either within the square material or prior to identifying the matrix, to enhance resolution of the image data. In one example, processor 108 employs a polynomial interpolation based on existing data units to fill in additional data units into a matrix to provide enhanced resolution. In such an example, the processor 108 may expand an N×N pixel square matrix, with N being an odd or even integer, into 4N×4N pixel square matrix. Through use of interpolation, a center of the region of interest may be more precisely located, and utilized as described below. Expansion of the matrix is commonly performed using bilinear or preferably bi-cubic interpolation, or potentially other methods.

In one or more examples, the region of interest is centered based on a 2D binary image blob-fit ellipse centroid, or center-fit of the gray-scale image data through use of an intensity-weighted center of mass calculation, the binary image blob and gray-scale image object having identical boundaries. Alternatively, the matrix may be un-centered on the image object, and/or include less than the entire image object. In one or more embodiments, the matrix may be padded with additional data units around the image object. For example, the matrix of FIG. 2B illustrates additional data units 115 surrounding the image object 114, while the matrix of FIG. 4B includes mask 111 to reduce the data units surrounding the image object 114. Alternatively, the image object may be clipped, by the boundaries of the matrix, to include only the matrix data closest to the center of the image object.

The matrix includes any number of data units. In the example of FIG. 2B, the matrix 107 includes approximately 180×180 pixels of image data. In the example of FIG. 3B, the matrix 127 includes approximately 90×90 pixels of image data. Each of the matrixes 107 and 127 is selected from image data having approximately 1000×750 pixels, as shown in FIGS. 2A and 3A. Depending on several factors (e.g., the size of an image object), any number of data units may be included in the matrix. A matrix may include from about 3×3 data units up to the entire captured image data, of the size that is provided from capture device 106. Furthermore, the matrix may be increased and/or decreased in size and/or resolution through one or more types of interpolation or sub-sampling. It should be understood that the size of the square matrix is a variable, which is selectable based on the amount of data to be processed by processor 108 within a time period suitable for inspection at high volume or medium volume manufacturing in various embodiments. For example, when used in a fabrication process of material 104, the amount of data included in the matrix may be selected to provide sufficient confidence, while permitting processing of the square image in less than about 1.0 second or another suitable time interval.

When the matrix is identified, processor 108 defines multiple halves of the matrix, which are defined by multiple different axes of the matrix. Several example halves and example axes of matrix 107 are shown in FIG. 5. Specifically, axis 200 extends vertically and defines a left half 208 and a right half 210 of matrix 107, while axis 202 extends horizontally and defines a top half and a bottom half. Further, axis 204 extends on a diagonal and defined a top-right half and a bottom-left half, while axis 206 extends on a diagonal and defines top-left half and bottom-right half. It should be appreciated that the axes and halves illustrated in FIG. 5 are for purposes of illustration and do not limit the number of orientations of axes and/or halves. As used herein, the term "half" generally refers to a substantially equal dissection of the matrix, within a substantially equal number of data units included in each of two halves. Minor deviations from exactly half the number of data units should be considered to be within the definition.

Further, as shown in this embodiment of FIG. 5, each of the axes 200, 202, 204, and 206 pass through the center 109 of the matrix 107. In this example, the center 109 of the matrix 107 is substantially the same as center 113 of the image object 114. The center of the matrix may be located otherwise, relative to the image object, in other embodiments.

With reference to vertical axis 200 of FIG. 5A, in this exemplary embodiment, processor 108 performs a flip of the matrix 107 about axis 200 and determines the difference between each data unit of the original matrix and a corresponding data unit of the flipped matrix. In another embodiment, processor 108 performs a fold of the matrix 107 about axis 200 and determining the difference between each data unit of the left half 208 and a corresponding data unit of the right half 210. The corresponding data unit includes a data unit on which a data unit would fall if the matrix 107 was physically folded and/or flipped onto itself, according to an axis, such as the axis 200. As shown in FIG. 5A, pixels 212A and 212B represent one pair of corresponding data units. If the intensity of a region of interest included in the matrix defines a symmetrical shape, the difference between the corresponding data points should be approximately zero. If, however, the region of interest is asymmetrical, several of the differences between corresponding data units will not be substantially zero.

The difference calculation used accumulates all differences with the same sign, for example all differences are accumulated as positive values, so that any image difference adds to the magnitude of the accumulation. For example, to achieve same sign differences, the accumulation may be performed using the absolute value of per data unit differences or the square root of the per data unit differences squared. Other approaches to achieving the same sign of the per data unit differences or operations of the differences are also contemplated. One such operation includes accumulating the squared differences as a sum of corresponding data units, dividing that sum by the number of differences summed, then taking the square root of that quotient. This is referred to as the root mean square (or RMS) of the differences. It should be understood that other linear or non-linear weightings of differences are also within the scope of the present disclosure.

Specifically, for example, as shown in FIG. 2A, the image object 114 or anomaly within the image data 118 is substantially circular. Accordingly, when the matrix 107 is folded over the vertical axis 200, the differences of each of the corresponding data units is shown in FIG. 2C. Because the image object 114 is not perfectly circular with a clean transition from inside to outside of the image object 114, some differences have a magnitude other than zero, as shown in FIG. 2C. In contrast, as shown in the example of FIG. 3A, the image object 124 within the image data 128 is substantially non-circular. Accordingly, when the matrix 127 is fold over its vertical axis, at least a portion of differences of each of the corresponding data units have magnitudes substantially above zero, as shown in FIG. 3C. Because the image object 124 (or anomaly) is non-circular and non-symmetric, the differences of intensity are greater than the difference shown in FIG. 2C. In this manner, to detect an APK based on the circular shape of the APK, processor 108 is able to determine the difference between corresponding data units in halves of a matrix, as an indicator of the symmetry of the region of interest. Note that due to symmetry the same-sign accumulation of differences can be performed across the entire matrix when the matrix is flipped, and can be performed across half of the matrix when the matrix is folded onto itself. In several examples, such accumulations differ by a factor of two and/or nearly two.

Further, processor 108 calculates an index value based on the accumulated differences of the corresponding data units of the two halve and stores the index value in memory 110. The index value is then used, either alone or in conjunction with other metrics of the data matrix or original image data, to identify an APK. The index value may be compared to a predetermined threshold and/or may be included in a more complex function of metrics of the matrix and/or original image. In this embodiment, processor 108 determines the RMS of the differences between the corresponding data units, which provides the index value. The index value may be further normalized based on the mean value of the matrix data units involved in the difference calculations so that the brightness and/or darkness of the underlying image does not impact the index value sufficiently to affect the conclusion of the index value. The RMS process has already removed the impact of the matrix size, but other accumulations of the differences between the corresponding data units may be considered suitable matrix size normalization steps. In another example, the index value may be provided from a dot-product of each of the differences of the corresponding data units. The dot product is accumulated and normalized by the number of data units relied on in the dot product accumulation. One or more other methods may be used to combine the differences of the corresponding units for comparison to a predetermined threshold, or thresholds, for determining either image judgment as APK, not APK, or potential APK, or for sample dispensation as PASS, FAIL, or REVIEW, if further, more detailed analysis may be necessary. In one or more embodiments, the predetermined threshold or thresholds are based on empirical data collected from multiple uses of the methods described herein on materials known to include APK and non-APK anomalies. The predetermined thresholds can further be adjusted upward or downward to change the confidence in the identification of APKs. Typically multiple metrics of the matrix and/or original image are used to most clearly identify APK-like images from images that are not likely to be APK. In some cases, other images at higher resolution may be required, or other metrology techniques may be used, prior to the final classification of the anomalies. This method may be applied, in some embodiments, to lower resolution and higher resolution images of the anomalies.

Furthermore, in various embodiments, processor 108 calculates multiple index values based on multiple axes of the matrix and store the multiple index values in memory 110. In this embodiment shown in FIG. 5, four index values are determined for each pairs of halves or each pair of matrixes (flipped and original). Specifically, an index value is calculated for the differences of corresponding data units for each of the left/right halves, top/bottom halves, the top-right/bottom-left halves and the top-left/bottom-right halves. In this manner, processor 108 substantially limits the potential for misidentifying an APK for a substantially symmetric shape, such as, for example, a cross or a diamond. It should be appreciated that multiple different axes oriented in a variety of different directions may be used to determine multiple different index values. The number and orientations of the axes are generally selected to provide at least a threshold level of confidence in detecting an APK, rather than a piece of debris or other non-APK anomalies within material 104.

When multiple index values are calculated, the identification of the APK is based on a combination of the multiple index values, as compared to the predetermined value. In this embodiment, each of the index values for the four axes are added together to provide a total index value for the matrix. The mean and maximum index values are also potentially useful metrics of the matrix. The predetermined threshold is provided to indicate whether the total index value is indicative of an APK or a non-APK anomaly in the material 104. Additional information may be further included, prior to comparison to a predetermined threshold. In one example, a ratio of the long radius to a short radius of an ellipse is added to the multiple index values. The ellipse may be based on the binary blob image, such as a best-fit ellipse, for example using the method of moments of the found anomaly image blob. Other values or metrics indicative of the attributes of the image object or binary blob may be further included to enhance the accuracy of detection of APK and non-APK anomalies.

In this embodiment, after the one or more fold/difference or flip/difference operations, processor 108 may normalize the image representative of the differences (e.g., FIGS. 2C and 3C) to account for the 2-dimensional size of the region of interest and/or the intensity of the region of interest. More specifically, in this embodiment, normalizing the image may include dividing the index value by a total number of pixels and/or dividing the index value by average intensity. A variety of different operations may be provided to normalize the image data and/or index value to provided accurate comparison to a single predetermined threshold. More generally, the data for each material 104 is processed sufficiently so that the three dimensional (3D) shape of the image object controls the determination of whether the image object is an air pocket, or something else. Intensity and size may contribute to the determination, but the 3D shape is the main characteristic under test, through the operations described herein. Normalization of the image data occurs after the folding or flipping operations in this exemplary embodiment, but may be completed prior to one or more folding operations in other embodiments.

It should be appreciated that one or more aspects of the present disclosure transform a general-purpose computing device into a special-purpose computing device when configured to perform the functions, methods, and/or processes described herein.

Embodiments herein may be described in the general context of computer-executable instructions, such as program components or modules, stored on one or more non-transitory computer-readable storage media and executed by one or more processors. Aspects described herein may be implemented with any number and organization of components or modules. For example, aspects of the disclosure are not limited to the specific computer-executable instructions or the specific components or modules illustrated in the figures and described herein. Alternative embodiments of the invention may include different computer-executable instructions or components having more or less functionality than illustrated and described herein.

The order of execution or performance of the operations in the embodiments illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of the present disclosure or the embodiments thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawings shall be interpreted as illustrative and not in a limiting sense.

What is claimed is:

1. A computer-implemented method for use in detecting an air pocket in a single crystal material, said method comprising:
providing a matrix including a plurality of data units, the plurality of data units including image data related to a region of interest of the single crystal material;
determining, by a processor, a difference between data units of the matrix and corresponding data units of the matrix, wherein the corresponding data units are defined by a first operation on the matrix performed about a first axis of the matrix;
calculating, by the processor, a first index value based on the differences between data units of the matrix and corresponding data units of the matrix;
calculating, by the processor, a second index value based on a second operation on the matrix, the second operation including one of a flip operation and a fold operation about a second axis of the matrix; and
identifying an air pocket within the single crystal material based on the first index value, the second index value, and a predetermined threshold.

2. The method of claim 1, wherein the first operation includes a flip operation about the first axis of the matrix.

3. The method of claim 1, wherein the first operation include a fold operation about the first axis of the matrix, whereby the plurality of data units are included in a first half of the matrix or a second half of the matrix.

4. The method of claim 1, further comprising interpolating the image data to provide the plurality of data units of the matrix.

5. The method of claim 1, further comprising identifying a blob of data units within an image of the single crystal material as the region of interest.

6. The method of claim 1, further comprising at least one of padding the region of interest with additional data units to provide the matrix and clipping data units from the region of interest to the matrix.

7. The method of claim 1, further comprising normalizing at least one of the matrix and the first index value based on at least one of the size of the matrix and an intensity associated the region of interest.

8. The method of claim 1 further comprising:
calculating a third index value based on a third operation of the matrix, the third operation including one of a flip operation and a fold operation about a third axis of the matrix; and
calculating a fourth index value based on a fourth operation of the matrix, the fourth operation including one of a flip operation and a fold operation about a fourth axis of the matrix, wherein identifying an air pocket within the single crystal material comprises identifying an air pocket within the single crystal material based on the first index value, the second index value, the third index value, the fourth index value, and a predetermined threshold.

9. The method of claim 1, wherein providing the matrix includes locating a square matrix on a portion of the image data including the region of interest.

10. The method of claim 9, wherein locating the square matrix includes substantially centering the square matrix on the region of interest.

11. The method of claim 1, further comprising normalizing at least one of the matrix and the first index value based at least in part on an intensity associated with the image data.

12. The method of claim 1, further comprising normalizing at least one of the matrix and the first index value based at least in part on a size of the region of interest.

13. The method of claim 1, wherein the single crystal material includes one of a silicon material, a germanium material, and a gallium arsenide material.

14. A detection system for use in detecting air pocket within a material, said detection system comprising:
- a light source configured to emit near-infrared (NIR) light toward a material;
- a detection device positioned adjacent to the material to capture image data based on light passing through the material; and
- a processor coupled to said light source and said detection device, said processor configured to:
  - identify a square matrix including a plurality of data units, the plurality of data units including the image data related to a region of interest of the single crystal material;
  - determine a difference between data units of the matrix and corresponding data units of the matrix, the corresponding data units defined by a first operation on the matrix performed about a first axis of the matrix;
  - calculate a first index value based on the determined differences;
  - calculate a second index value based on a second operation on the matrix, the second operation including one of a flip operation and a fold operation about a second axis of the matrix; and
  - identify an air pocket within the single crystal material based on the first index value, the second index value, and a predetermined threshold.

15. The detection system of claim 14, wherein the first operation includes a flip operation about the first axis of the matrix.

16. The detection system of claim 14, wherein the first operation includes a fold operation about the first axis of the matrix, whereby the plurality of data units are included in a first half of the matrix or a second half of the matrix.

17. The detection system of claim 14, wherein said processor is further configured to normalize at least one of the square matrix and the index values based on at least one of a size of the square matrix and an intensity associated the region of interest.

18. The detection system of claim 14, wherein said processor is configured to determine the root-mean-square of the differences of the corresponding data units to calculate the first index.

19. The detection system of claim 14, wherein the plurality of data units include a plurality of pixels.

20. The detection system of claim 14, wherein the single crystal material includes one of a silicon material, a germanium material, and a gallium arsenide material.

21. The detection system of claim 14, wherein said processor is configured to substantially center the square matrix on the region of interest.

22. One or more non-transitory computer-readable storage media having computer-executable instructions embodied thereon, wherein when executed by at least one processor, said computer-executable instructions cause the at least one processor to:
- identify a matrix including a plurality of data units, the plurality of data units including image data related to a region of interest of the single crystal material;
- determine a difference between data units of the matrix and corresponding data units of the matrix, wherein the corresponding data units are defined by a first operation on the matrix preformed about a first axis of the matrix;
- calculate a first index value based on the differences between data units and the corresponding data units;
- calculate a second index value based on a second operation on the matrix, the second operation including one of a flip operation and a fold operation about a second axis of the matrix; and
- identify an air pocket within the single crystal material based on the first index value, the second index value, and a predetermined threshold.

23. The non-transitory computer-readable storage media of claim 22, wherein the computer-executable instruction further cause the processor to normalize at least one of the matrix and the first index value based on at least one of a size of the matrix and an intensity associated the region of interest.

24. The non-transitory computer-readable storage media of claim 22, wherein the computer-executable instruction further cause the processor to determine the root-mean-square of the differences between the data units and the corresponding data units in order to calculate the first index.

* * * * *